(12) United States Patent
Kiefersauer et al.

(10) Patent No.: US 6,355,217 B1
(45) Date of Patent: Mar. 12, 2002

(54) HOLDING DEVICE FOR PARTICULATE SAMPLES

(75) Inventors: Reiner Albert Kiefersauer, Munich; Robert Huber, Germering, both of (DE)

(73) Assignee: Max-Planck-Gesellschaft, zur Forderung der Wissenschaften e.V. (DE)

( * ) Notice: Subject to any disclaimer, the term of this patent is extended or adjusted under 35 U.S.C. 154(b) by 0 days.

(21) Appl. No.: 09/395,865

(22) Filed: Sep. 17, 1999

(30) Foreign Application Priority Data

Sep. 18, 1998 (DE) .......................................... 198 42 797

(51) Int. Cl.[7] ................................................. B01L 3/00
(52) U.S. Cl. ........................ 422/102; 422/99; 422/104; 422/939
(58) Field of Search ............................. 422/58, 59, 99, 422/102, 103, 104, 939, 940, 947; 435/283.1, 287.1, 288.7

(56) References Cited

U.S. PATENT DOCUMENTS 4,728,135 A  3/1988 Sugimura et al. .......... 294/64.1
5,494,641 A * 2/1996 Krstanovic ................. 422/103

FOREIGN PATENT DOCUMENTS

CH            481726          11/1969

OTHER PUBLICATIONS

Hope, H., "Cryocrystallography of Biological Macromolecules: a Generally Applicable Method", *Acta Cryst.* vol. B44, pp. 22–26, 1988.

Kiefersauer, R. et al., "Protein–Crystal Density by Volume Measurement and Amino–Acid Analysis", *J. of Applied Crystallography*, vol. 29, pp. 311–317, 1996.

* cited by examiner

Primary Examiner—Maureen M. Wallenhorst
(74) Attorney, Agent, or Firm—Pepper Hamilton LLP; Robert A. Koons, Jr.; Matthew P. McWilliams

(57) ABSTRACT

A holding device for particulate material samples features a carrier block for a holding a capillary or a loop holder that has a free mounting end for a particular sample, whereby the carrier block includes at least one integral gas channel with an opening end that is directed at the mounting end of the holding capillary or a loop holder.

11 Claims, 4 Drawing Sheets

HOLDING DEVICE FOR PARTICULATE SAMPLES

FIELD OF THE INVENTION

The subject of the invention is a holding device for particulate material samples, especially a sample holder for particles with high fluid content like protein crystals.

BACKGROUND OF THE INVENTION

Protein crystallography is a technique for analyzing the structure of proteins in which the latter are exposed to X-ray or synchrotron radiation in a crystallized state to enable conclusions about the molecular structure from diffraction patterns. The size and the irregular form of the protein molecules mean that protein crystals are characterized by very slight lattice forces and high solvent content in the region of 30 to 70% or even as much as 90%. Consequently protein crystals are unstable and restricted to characteristic crystal sizes between 0.003 mm and 1 mm. This instability is seen especially in the loss of crystal structure as soon as the crystal loses solvent through removal of water at room temperature.

It is generally known that protein crystals can be analyzed in a sealed capillary in the presence of free solvent to achieve adequate stability during structural analysis. A virtually saturated solvent atmosphere forms in the capillary, which prevents the crystallites from desiccating or drying. The disadvantage of this technique is that the crystallites in the capillaries are difficult to manipulate and that low-temperature treatment as protection against radiation damage in the protein crystal during structural analysis, as described for example in the publication by H. Hope in "Acta Cryst." (vol. 44, 1998, p 22 ff), is restricted in its application.

A holder for single protein crystals is described by R. Kiefersauer et al. in "J. Appl. Cryst." (vol. 29, 1996, p 311 ff). The conventional holder for the so-called free mounting system shown in FIG. 7 comprises in particular a holding capillary 41 arranged in a carrier block 42. One end of the holding capillary 41 is connected to a suction device (not shown) so that the inside of the holding capillary 41 can be subjected to a low pressure. The other end, projecting from the carrier block 42, forms a mount for the protein crystal. The advantage of this holder is that single protein crystals can be manipulated in the beam of the analyzer device. Nevertheless, special precautions are necessary to maintain crystal stability that restrict possibilities of manipulating the holder acting as a sample head. On the holder of the protein crystal at the end of the holding capillary 41, the crystal structure would change or dissolve rapidly at normal room conditions through the removal of solvent. For this reason a holder of this kind is operated in conjunction with a humidity feed (not shown in FIG. 7) where a humid stream of air is conducted to the held protein crystal through jets for example. The disadvantage of the humidity feed by separate jets is the more difficult manipulation of the holder, because the humidity jets have to be moved simultaneously without shadowing radiation of the crystal for instance.

A further disadvantage of the conventional humidity feed with jets is the more difficult control of the stream of gas actually exiting from the jets in relation to its humidity and flow conditions.

The indicated problems in holding protein crystals also occur in the manipulation of other particulate material samples with a high fluid content. These include biological objects like biological cells or cell constituents, and synthetic non-crystalline objects with a high solvent content. If objects of this kind are to be analyzed free of surrounding solvent, desiccation problems occur as described above in the case of protein crystals.

SUMMARY OF THE INVENTION

An object of the invention is to provide an improved holding device for particulate material samples with high fluid content that allows simplified manipulation of the samples, especially in analytical instruments and without restricting measurement functionality. Another object of the invention is also to propose novel and improved uses of such a holding device.

These objects are generally solved by a holding device for material sample particles with a carrier block for a holding element comprising e.g. a holding capillary or a loop holder, that has a free mounting end for a particulate sample, wherein the carrier block includes at least one integral gas channel with an outlet end that is directed at the mounting end of the holding element.

Accordingly, a holding device with a carrier block is created that includes not only a holding capillary, functioning in the way of vacuum pincers for example, or a loop holder but also at least one integrated gas channel that is directed at the mounting end of the holding capillary or the loop holder. The gas channel exits adjoining the holding element so that a local atmosphere is formed at the end thereof from gas or vapor flowing out of the gas duct. in a preferred implementation of the invention, the gas channel has an inner diameter that is greater than the outer diameter of the holding element, the latter being passed through the center of the gas channel so that the gas or vapor is fed through the gas channel in the remaining cylindrical space between the holding element and the edge of the gas duct. The holding capillary is surrounded by the gas duct.

In an especially advantageous or preferred form, the holding device according to the invention consists of a head part and an insert. The head part contains the gas channel, which a t the same time forms a lead-through for the holding capillary or the loop holder. The head part also forms a receptacle for the insert so that the latter can be shifted axially in the head part and fixed at a certain position. In this way the spacing of the end of the holding capillary or the loop holder, which forms a support for the particular material sample, from the exit of the gas channel or the surface of the carrier block can be altered in a predetermined way.

In the context of what is described here, a carrier block is any mechanical structure that allows the positioning and/or movement of a holding capillary or a loop holder. The holding capillary can be a hollow capillary operated with a vacuum (vacuum tweezer) or a compact, extended, pointed component with a support at its end for the particular material sample. Thus the invention is not restricted to implementation with the vacuum tweezer structure but can also be used with other holder devices in which the particulate material sample adheres to the tip of the holding capillary through the effect of adsorptive forces, electrical forces or an adhesive. An example for such an alternative holding device is the loop holder noted above which comprises a base part, a support part and the loop as such. Loop holders of this kind are known from protein crystallography or cryotransferring of samples. The term gas channel comprises every kind of gas feeder line. Several gas ducts may also be provided. The gas conducted in the gas channel will be, depending on application, a gas or a vapor with a certain content of vaporous substances that correspond to the fluid and/or added substances contained in the particular material sample. Thus it is possible for instance, to maintain certain surface properties on the material sample, to conduct a vaporous substance through the gas channel that differs from the fluid or solution in the sample.

The invention is associated with the following advantages. The carrier block of the invention with integrated gas channel allows improved and controlled manipulation of the sample. The disadvantage of shadowing in the measurement system through separate gas jets is avoided. The gas channel allows homogeneous and uniform feeding of the gas. Complete inclusion of the sample is guaranteed in all positions of the mounting device. Precise alterations of the sample are simplified. This affects both feeding added substances through the gas channel and the above mentioned low-temperature treatment, for example, as protection against radiation damage in protein crystals. The holding device according to the invention can be miniaturized. In an axial-symmetrical arrangement of the holding element, this will automatically be centered in the gas stream. The structure of the holding device according to the invention allows simplified adjustment in relation to a measurement setup. The number of interfering (e.g. scattering) components in the measurement range is reduced. The mounted sample is better accessible for additional measurement procedures (e.g. optical measurements).

For the first time the invention allows defined temperature setting in particulate material samples by setting the gas stream in the carrier block to a defined temperature. The sample immediately assumes the temperature of the gas because of its smallness in size. In this connection it should be emphasized that the gas conducted in the gas channel can also be an inert gas without added vapor and that this inert gas only exercises a tempering or even application-specific drying function.

BRIEF DESCRIPTION OF THE DRAWINGS

Further advantages and details of the invention will be described in what follows with reference to the drawings, which show.

DETAILED DESCRIPTION OF THE INVENTION

The invention is described below taking the protein crystal holder as an example, but can also be implemented in analogous fashion to hold other particulate sample materials, especially biological or synthetic materials as indicated above.

Figure 1:
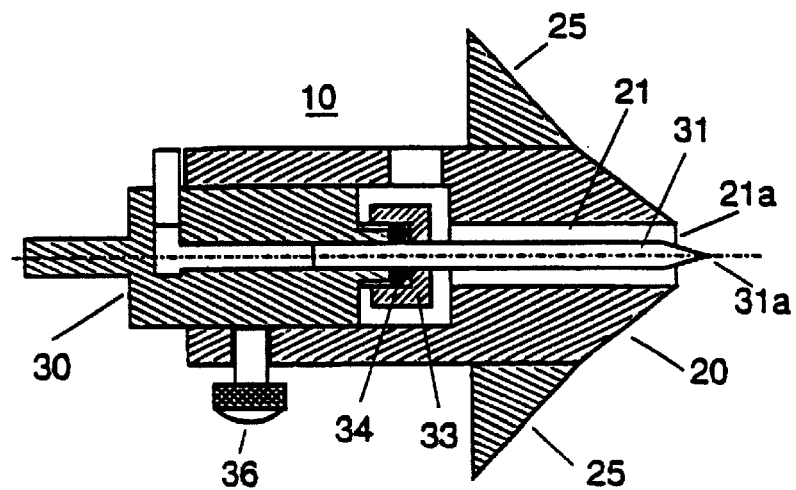
FIG. 1 a sectional view of a first embodiment of the holding device according to the invention, FIG. 2 a sectional view of a head part of the holding device according to FIG. 1, FIG. 3 a sectional view of the insert of a holding device according to FIG. 1, FIG. 4 a sectional view of a second embodiment of the holding device according to the invention, FIG. 5 a partial longitudinal and a front view of the insert of the holding device of FIG. 4, FIG. 6 a sectional view of a third embodiment of a holding device according to the invention with a schematic cross-sectional view of the head part of this holding device, FIG. 7 a sectional view of a conventional holding device, and FIG. 8 a schematic of a conventional arrangement for generating a humid gas stream.

FIG. 1 shows a holding device according to the invention, exemplified by a holder for protein crystals in a sectional view. The crystal holder comprises a carrier block 10 with a head part 20 and an insert 30 that are shown separately in part in FIGS. 2 and 3. The head part 20 is a solid component with one bore for the gas channel 21 and a second bore for the insert receptacle 22. The bores are axially aligned with one another. The gas channel 21 is connected to a gas source (not shown) by part of the insert receptacle 22 and by the side duct 23. The side duct 23 is essentially at right angles to the axial direction of the gas channel 21 and the insert receptacle 22 and exits in the latter at the end towards the gas duct. The head part 20 also has a side opening 24 leading out from the insert receptacle 22 and designed to hold the setting element 36.

The gas channel 21 runs straight from the insert receptacle 22 to the exit on the conically tapered surface of the head part 20 at the measuring apparatus end. The end of the gas channel 21 has an exit 21a (outlet 21a) directed at the mounting end 31a of the holding capillary 31.

Figure 3:
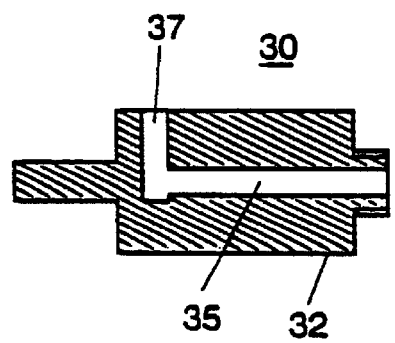

The insert 30 is intended as a carrier for the holding capillary 31 (see FIG. 1) and comprises a base 32 and a sealing part 33. The base 32, shown in detail in FIG. 3, is a molded part with a central bore intended as a capillary receptacle 35. The capillary receptacle 35 is connected to a vacuum duct 37 that, in the example shown, exits from the insert 30 essentially at right angles to the capillary receptacle 35. The vacuum duct 37 is connected to a pumping device (not shown) through a vacuum line. In the assembled condition of the insert 30, the holding capillary 31 is inserted in the capillary receptacle 35. The inner diameter of the capillary receptacle 35 is preferably a form-fit match with the outside of the holding capillary 31 on its outer diameter. But there may also be slight clearance, because the sealing part 33 is provided with a ring seal 34 to prevent pressure loss from inside the holding capillary 31 or capillary receptacle 35 to the gas channel 21.

The holding capillary 31 preferably consists of a glass tube or micropipette (diameter approx. 1 mm) with an extended tip. Production of the holding capillary 31 follows what is called the patch-clamp technique. After extruding a glass tube, a tip diameter in the $\mu$m region is produced. In the area of the required tip diameter, the tip is broken off and ground to create as flat as possible a ring mounting surface for the protein crystal. The diameter selected for the tip of the micropipette depends on the size of the protein crystal and can be about 0.1 to 0.3 mm for example. But the diameter may be chosen smaller for especially small protein crystals (down to 30 $\mu$m). The mounting is made with a vacuum in the capillary of about 0.05 to 0.2 bar.

The sealing part 33 is a cap with an axial bore set on the shoulder of the base 32, this bore being aligned with the capillary receptacle 35 and serving to position the holding capillary 31 and seal the capillary receptacle 35. The ring seal 34 is attached between the sealing part 33 and the shoulder.

The sealing part 33 interacts as follows with the base 32. The holding capillary 31 is pushed through the bore of the sealing part 33 and set with this on the shoulder of the insert 30 at the head end together with the ring seal 34 (e.g. of rubber). Between the sealing part 33 and the shoulder there is a screwed connection (not shown) so that the sealing part 33 can be fastened on the shoulder like a screw-down cover. Alternatively it is possible that the sealing part 33 will already be seated loosely on the shoulder and that the holding capillary 31 is pushed through the hole of the seated sealing part 33. The ring seal is compressed as a result of screwing tightly. The sealing material faces with all adjoining surfaces of the capillary and insert and sealing part so that the capillary receptacle 35, and thus the inside of the capillary are sealed off from the gas duct.

The base 32 with the seated holding capillary 31 is inserted in the insert receptacle 22 of the head part 20. The insert 30, depending on the required use, is pushed into the insert receptacle 22 so that the extended tip of the holding capillary 31 with the mount for the protein crystal remains sunken in the gas channel 21 or projects from the exit of the gas channel 21 by a predetermined amount. Three uses are considered for example. In transport status the holding capillary is retracted in the gas duct. The tip of the holding capillary 31 is covered by the head part. In flow status the tip will project from the exit by about 1 to 5 mm for instance. In the low-temperature treatment status (without the humid gas stream) the tip can project more from the exit (e.g. by about 20 mm). In the required position the insert 30 is fixed with the setting element 36. Then the vacuum line is connected to the vacuum duct 37 and the gas supply to the side duct 23 and a protein crystal (e.g. a CODH (carbon monoxide dehydrogenase) crystal) is picked up from a growth solution. The mounting device according to the invention is then ready for use and is attached with the head part 20 (possibly with a separate holder) or with the insert 30 to the goniometer head of an X-ray or synchrotron radiation apparatus for example.

The holding capillary 31 may alternatively be connected (e.g. adhered) firmly and gas tight to the sealing part 33 and/or the base 32.

Figure 2:
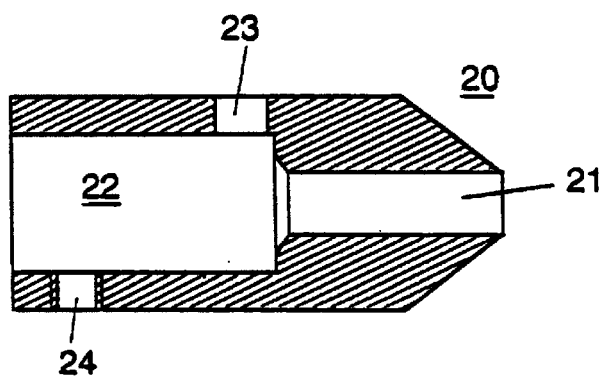

The parts of the holding device 10 according to the invention preferably consist of non-corroding material (e.g. plastic) of low thermal conductivity like Delrin or Teflon (registered trademarks). But other materials are possible depending on the application. Scaling will also be dependent on the application. The crystal holder 10 is shown in FIGS. 1 through 3 on a scale of about 2:1. Differing from the example, the proportions of the individual parts can be altered in relation to one another, although the gas channel 21 should still be at least about 15 mm in length. The length of the gas channel in the head part 20 is preferably chosen so that the solvent or added substance vapors fed in the gas distribute as homogeneously as possible. To produce as straight and undisturbed as possible an exit of the gas from the gas channel 21, the latter has a simple outlet end 21a on a flat surface of the head part 20. The sample on the mounting end 31a of the holding capillary 31 is enclosed entirely in the gas stream from the gas channel.

The outer form of the head part 20 is such that the particular measuring operation is impeded to a minimum degree. For this purpose the head part 20 tapers towards the measuring apparatus and the mounting end of the holding capillary so that, at the outlet of the gas channel 21, the outer diameter of the head part 20 is more or less the same as the outlet diameter of the gas channel 21. On the side of the measuring apparatus the head part 20 therefore forms a conical stump with an angle of inclination of about 35° referred to the conical axis.

FIG. 1 also shows the head part 20 with an integrated icing shield 25. This icing shield 25 is between the conical stump end of the head part 20 and the side openings and ducts on the cylindrical body of the head part 20. The icing shield 25 features special advantages for protecting the rear crystal holder parts in low-temperature treatment, as explained below.

As an additional icing shield and/or as a tempering device for the gas through the gas channel 21, a tempering device (see FIGS. 4–6) can be integrated into the head part 20. The tempering device can be an electric heating element, for example, or a flow system for conducting heating or cooling fluids, or a Peltier element. A heating element may be a filament wire in a spiral groove in the conical surface of the head part 20 and possibly attached or covered by silicon rubber. A sensor device—a humidity and/or temperature sensor or chemical sensors—can also be connected in the head part to the gas channel 21, preferably at its outlet end.

The structure in FIG. 1 can be modified so that the sealing part 33 is an integral part of the head part 20 and the insert receptacle 22 terminates at the gas channel end. In a design of this kind the holding capillary 31 projects through an axial bore in the sealing part 33, on the one hand through the gas channel as far as its outlet and beyond by the amount stated above, and on the other hand into the capillary receptacle of the insert 30. In this case the insert 30 can be provided with an outer thread to engage with an inner thread on the inner surface of the insert receptacle 22 of the head part 20. Here sealing is by a ring seal between the screwed-in insert and the integral sealing part.

Figure 4:
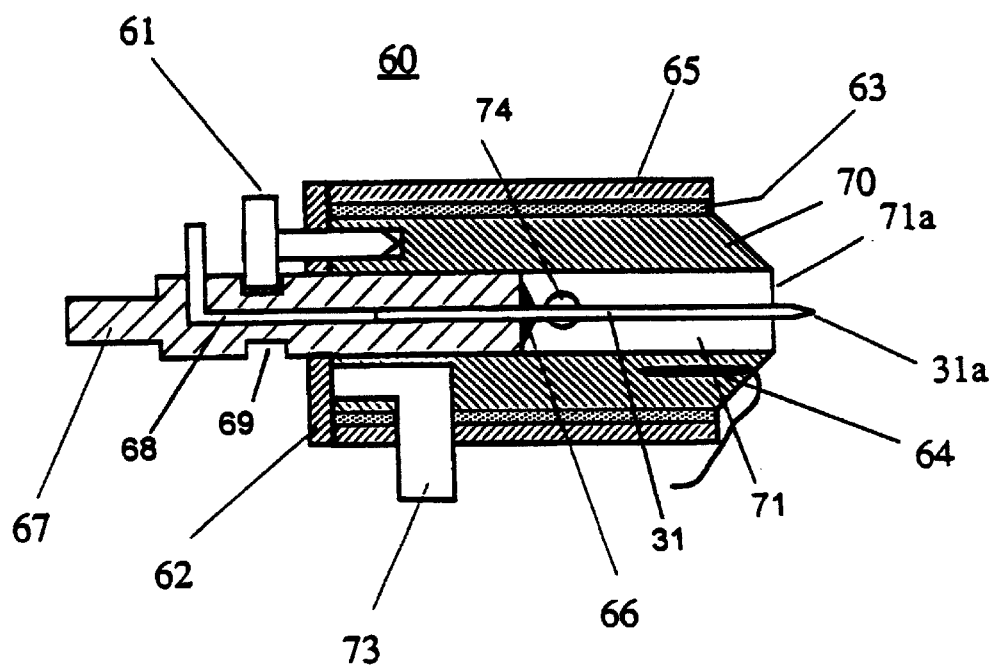
Figure 5:
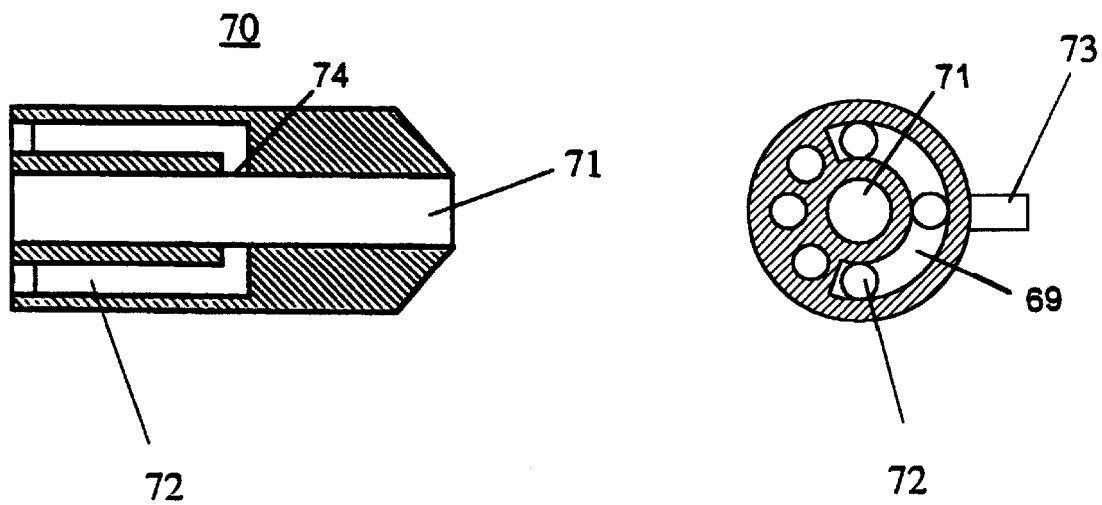

FIGS. 4 and 5 show a second embodiment of a holding device according to the invention. This embodiment also provides a crystal holder for protein crystals. As in the embodiment of claim 1, the crystal holder comprises a carrier block 60 with a head part 20 being illustrated with further details in FIG. 5 and an insert 67. The head part 70 has a through bore which forms on a first side the gas channel 71 and on the other side a receptacle for the insert 67. The gas channel 71 is connected via a-duct system in the head part 70 and a side duct 73 (tubing connection) with a gas source (not shown). The side duct 73 comprises a plurality of branches 72 in the head part 70 which directly exit t the openings 74 into the gas channel 71.

A heating element 63 and a temperature sensor 64 are integrated into the head part. Accordingly, a predetermined temperature can be set at the head part 70. The reference numeral 65 refers to an additional insulation layer which further improves the temperature control. As the branches 72 lead through the head part 70 with temperature control, an optimum temperature control of the gas stream is possible which is independent of possible temperature variations in the surrounding of the carrier block 60.

As in the embodiment illustrated above, the insert 67 is intended as a carrier for the holding capillary 31. The holding capillary 31 is placed in the insert 67 and sealed relative to the insert with a sealing 66 made from a glue or wax. Accordingly, a low pressure in the low pressure duct 68 can be transferred via the holding capillary 31 directly to the tip 31a thereof.

The position of the micropipette tip 31a and correspondingly of the sample (not shown) relative to the outlet 71a of the gas channel is set with the position screw 61. If the head part 70 and the insert 67 are positioned rotatably with regard to each other, the head of the position screw 61 is guided in a corresponding groove 69 of the insert 67 during the rotation.

Figure 6:
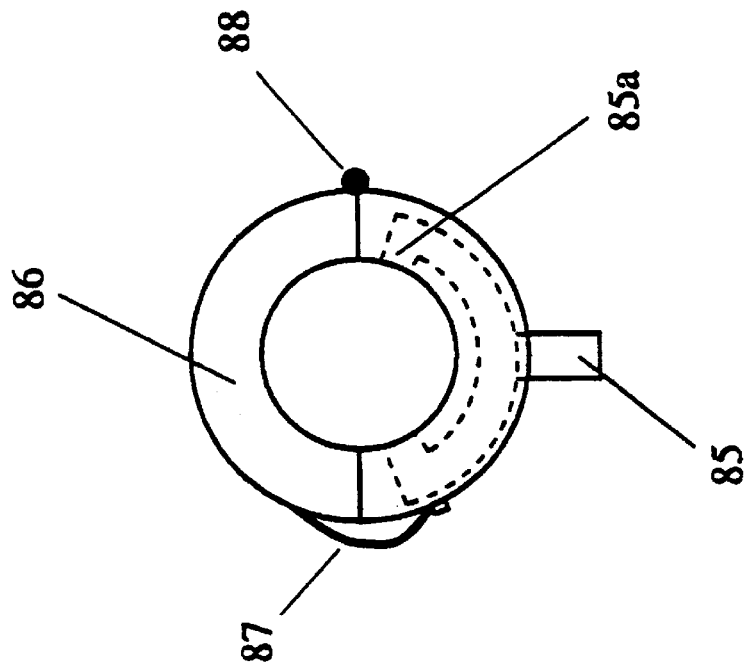
Figure 6:
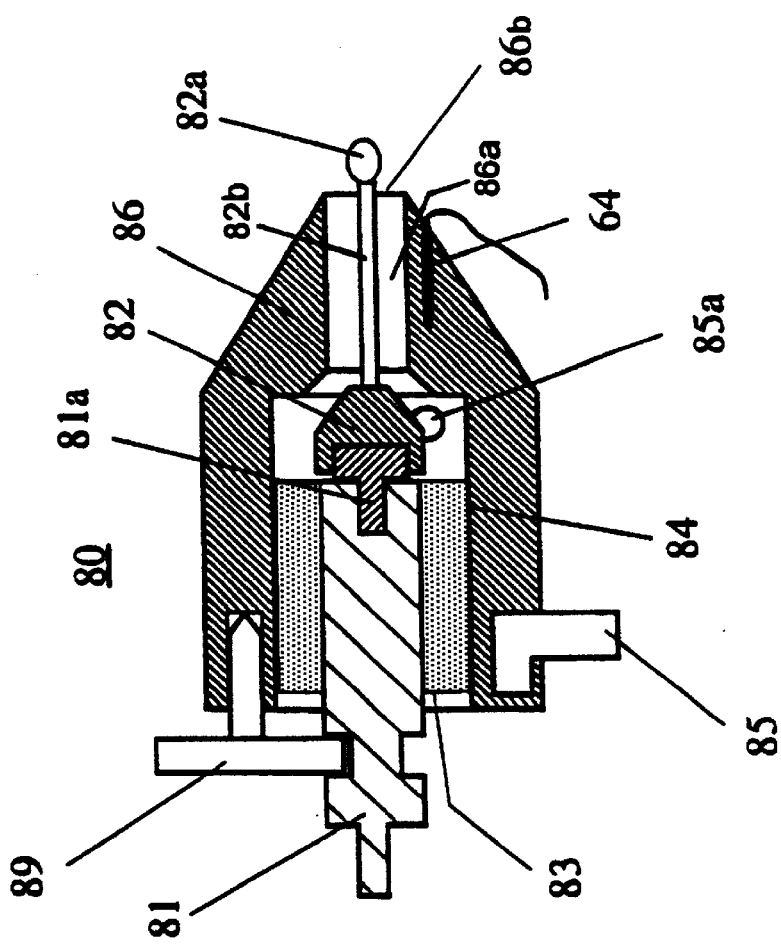
Figure 7:
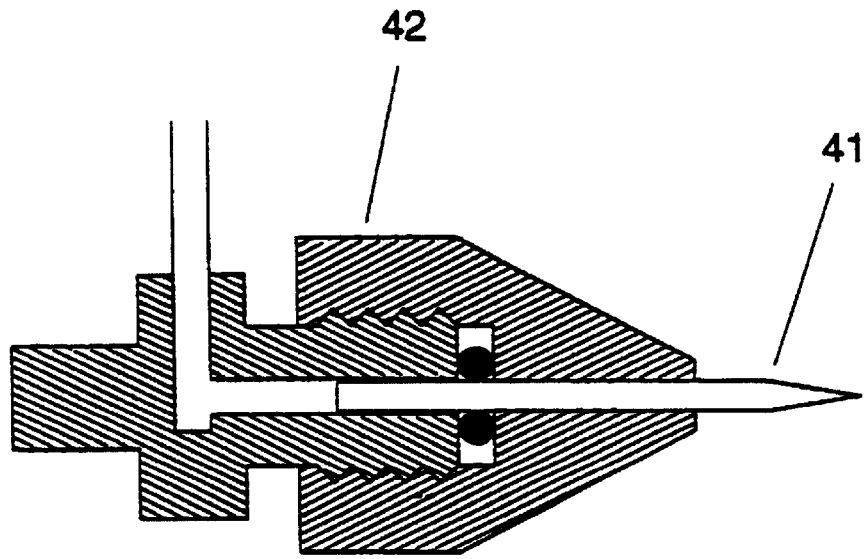

In FIG. 6, a third embodiment of the invention is illustrated wherein the holding element for holding the sample is provided by a loop holder. The left part of FIG. 6 shows a crystal holder with a carrier block 80 being structured with a head part 86 and an insert 81. The head part 86 is a compact component with two bores being axially aligned and adjacent to each other. The bores form on the first side the gas channel 86a with the outlet 86b and on the other side the receptacle for the insert 81.

The insert 81 is also a compact component due to the loop shape of the holding element as no low pressure duct is necessary. The insert 81 is rotatably supported on a needle bearing 83 in the head part 86. At the inner end of the insert 81, a magnetic holder 81a is provided on which the base 82 of the loop holder is positioned. The base 82 has an inner recess which is adapted to the outer shape of the magnetic holder 81a so that the loop holder is centered in the heat part 86.

The reference numeral 84 refers to a heating element which sets the temperature of the head part 86 and correspondingly of the gas stream in the side duct 87 to the gas channel 86a. The temperature of the head part 86 is monitored with a temperature sensor 64. The gas entering the head part 86 via the side duct 85 is guided through branches (shown in the right part of FIG. 6 with broken lines) to the corresponding exit opening 80a.

The loop 82a is connected with the base 82 via the carrier part 82b. The position of the loop 82a relative to the outlet 86b of the gas channel 86a is set with the position screw 89 the head of which protrudes into a group of the insert 81 as it has been described above. Accordingly, the head part is freely rotatable relative to the insert. This rotatability of the head part is an important feature of the holding device according to the invention as leads or supplies for the sample heat must not be damaged when the head part is rotated during the measurement of the sample.

The picking up of a particulate sample (e.g. protein crystal) with a loop 82a is known as such. Up to now it is used for the manipulation of samples for the cryo transfer thereof in protein crystallography. For ensuring such a cryo conservation, the holding device according to the invention is formed such that the loop holder can be taken out of the heat part 86 without problems. To this end, the heat part 86 is divided into two shells as it is illustrated in the right part of FIG. 6. The shells are connected via a joint 88. On the opposite side, the shells are gripped with the spring 87. By opening the spring connection, the shells can be opened and the loop holder can be taken by separating the base 82 from the magnetic holder 81a. Then the loop 82a is transferred into a tank with liquid nitrogen.

In the following further details of the gas supply into the gas channel of a holding device according to the invention are described.

Figure 8:
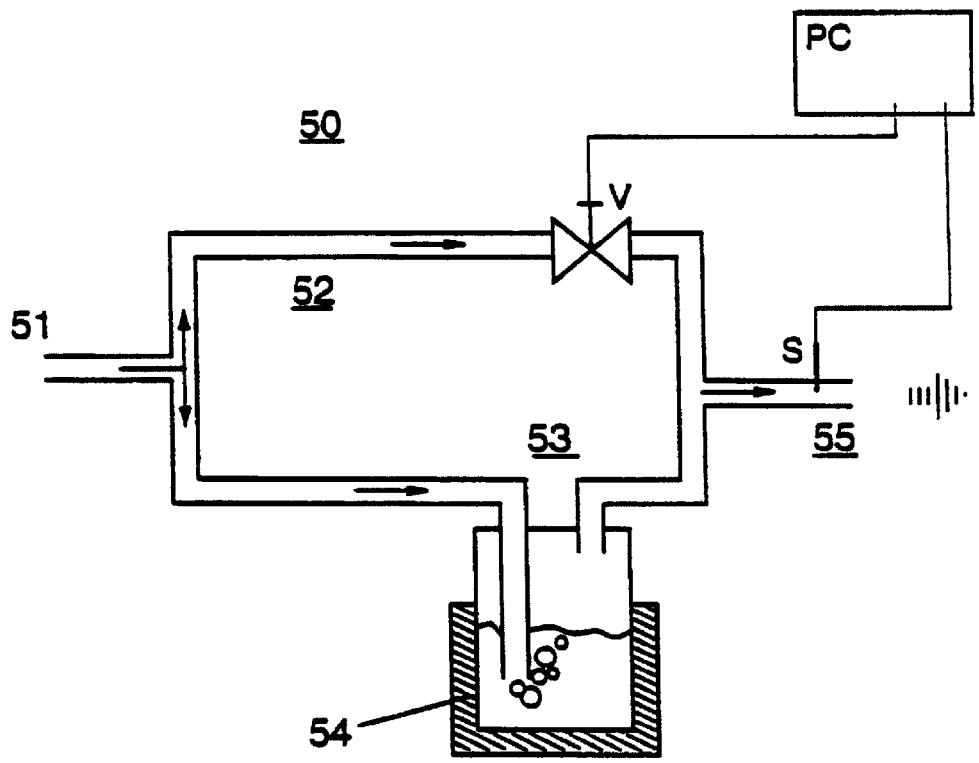

The gas supply into the gas channel 21, 71 or 86a can use a humidity regulating system, for example, as known from the above mentioned publication by R. Kiefersauer et al. (1996) and shown in FIG. 8. The publication by R. Kiefersauer et al. is introduced into this specification by reference concerning details of the humidity regulating system. The system 50 comprises a gas feed 51 that splits into a dry branch 52 and a humid branch 53. There is a computer-controlled valve V in the dry branch 52. The humid branch 53 initially leads into the water and/or added substance reservoir 54, in which the dry air is bubbled through water at an increased temperature.

After this the air in the humid branch 53 has a high humidity content (virtually saturation). After the valve V or water reservoir 54 the two branches are combined again. In the joint gas feed channel 55 there is a humidity sensor S, where the computer controls the valve V as a function of the sensor signal and predetermined values of humidity. The gas feed 55 is connected to the side duct 23 of the holding device according to the invention by a tubing. Instead of the sensor S, regulation is also possible with a humidity sensor in the gas channel 21 of the holding device (see above).

For implementation of the cryo treatment, which is known as such, a protein crystal mounted at the end of the holding capillary 31 is subjected to cooling. The cooling is preferably done by shock freezing with a cold, separately fed nitrogen gas stream at a temperature of about −170° C.

Further feeding of gas through the gas channel 21 is omitted. A deep cooled protein crystal is subjected to structural analysis in its cooled state by synchrotron or X-ray radiation.

An extra protective coat can be applied to the crystal as protection against desiccation (drying) in the cold stream. For this purpose a drop of protective solution is picked up with a wire or plastic loop, as already familiar, which is normally used itself for holding protein crystals, and transferred in the humid gas stream to the crystal in the holder device. The loop is passed back and forth over the capillary tip with the crystal so that at least some of the solution is retained by the crystal.

The holding device according to the invention allows the implementation of a new crystal transformation process as explained below.

The crystal transformation process comprises defined withdrawal of water from the protein crystal before structural analysis. It was determined for the first time that reproducible withdrawal of water from the crystal of up to 20% produces an increase in molecular order and thus a substantial improvement in analysis results. A protein crystal in the holding device, using a configuration according to FIG. 5, is subjected to a gas stream of reducing humidity following a fixed time pattern. The duration of humidity reduction is between 5 and 60 min depending on crystal size. This is followed by familiar structural analysis.

The crystal transformation process produces the following advantages. An increase in the maximum scattering angle and the signal/noise ratio at greater scattering angles was determined. Before transformation the greater scattering angles can only be evaluated to a limited extent. After transformation the reflexes at large angles are also of sufficient amplitude. The crystal transformation process also leads to reduction of the mosaicity of the crystallites from conventional figures in the region of about 1.5° to figures down to about 0.4°. High mosaicity is a disadvantage because, through tipping of crystallites, a lot of large spots appear that overlay one another and make analysis difficult. Other parameters that are of interest in crystallography when evaluating diffraction patterns and improve considerably when using the holding device according to the invention are the so-called B factor, the intensity of the diffraction orders and the scattering angles.

The holding device according to the invention can be used in addition to or beside structural analysis to expose the mounted protein crystal to pulsed changes in humidity, which cures structural defects. This "annealing" can be implemented to special advantage with the holding device according to the invention because the temperature and humidity of the gas stream in the gas channel 21 can be set with high reproducibility and accuracy. If the holding device according to the invention is used to mount particles of organic molecules, substances with a high water content, sacchariferous substances, hydrated or dehydrated substances or polymer polysaccharides, the size of the tip of the holding capillary 31, of the gas channel 21, of the gas vacuum in the holding capillary 31 and the composition of the applied gas would be adapted accordingly.

The holding device according to the invention can be modified for a large number of gas ducts instead of one gas channel 21 with the holding capillary 31. These could run through the head part spaced from the holding capillary for example. These gas ducts would preferably be straight but inclined to the reference axis formed by the holding capillary so that the exit ends of these gas ducts are jointly directed at the mounting end of the holding capillary. In a further modification it is possible to construct the holding device according to the invention with a single-piece carrier block—instead of a multi-part carrier block—in which the holding capillary and at least one gas channel are held or formed.

We claim:

1. A holding device for a particulate material sample, the device comprising;

a holding element and a carrier block for receiving the holding element, the holding element having a first end for inserting into the carrier block and a second mounting end for supporting a particulate sample, the carrier block having at least one gas channel therein, the gas channel having an outlet end, wherein, a flow of gas in the gas channel is directed to the second mounting end of the holding element and the outlet end is proximate to the second mounting end of the holding element when the holding element is inserted into the carrier block, and a gas flowing through the at least one gas channel towards the outlet end creates a local atmosphere of the gas in a region proximate to the outlet end of the channel, wherein, the second mounting end of the holding element is located in the region.

2. The holding device according to claim 1, in which the carrier block comprises a head part and an insert, the head part having an insert receptacle for receiving the insert, and the insert having a holding element receptacle for receiving the first end of the holding element, the at least one gas channel defining an axial bore through the head part, such that when the insert is inserted into the insert receptacle, the holding element passes through the axial bore.

3. The holding device according to claim 2, in which the insert is axially movable in the insert receptacle and can be fixed to a predetermined position by a setting element so that the mounting end of the holding element is sunken in the head part or projects from the head part by a predetermined extent.

4. The holding device according to claim 3, in which the projection of the mounting end is selected between about 1 and about 5 mm.

5. The holding device according to claim 2, in which an icing shield is provided on the head part.

6. The holding device according to claim 2, in which there is a tempering device provided in the head part.

7. The holding device according to claim 2, wherein the head part is freely rotatable relative to the insert.

8. The holding device according to claim 2, in which a gas stream through the gas channel is provided via branches being integrated in the head part.

9. The holding device according to claim 1, in which a temperature sensor and a humidity sensor are attached to the outlet end of the gas channel.

10. The holding device according to claim 1, wherein the holding element is a holding capillary or a loop holder.

11. A method for manipulating a particulate sample, the method comprising;

providing a holding device comprising; a holding element and a carrier block for receiving the holding element, the holding element having a first end for inserting into the carrier block and a second mounting end for supporting a particulate sample, the carrier block having at least one gas channel therein, the gas channel having an outlet end, wherein, the outlet end is proximate to the second mounting end of the holding element when the holding element is inserted into the carrier block, introducing a particulate sample into the second mounting end of said holding device, and flowing a gas through the at least one gas channel towards the outlet end to create a local atmosphere of gas in a region proximate to the outlet end of the channel where the second mounting end of the holding element is located.

* * * * *